United States Patent [19]

Janko

[11] 4,357,945
[45] Nov. 9, 1982

[54] DEVICE FOR TESTING AND RUPTURING AMNIOTIC MEMBRANE

[76] Inventor: Albert B. Janko, 977 Pacific St., Monterey, Calif. 93940

[21] Appl. No.: 269,578

[22] Filed: Jun. 1, 1981

[51] Int. Cl.³ .......................... A61B 5/10; A61F 13/00
[52] U.S. Cl. .............................. 128/771; 128/303 R ; 128/307 ; 128/361
[58] Field of Search .................. 128/771, 307, 303 R, 128/361, 759, 253

[56] References Cited

U.S. PATENT DOCUMENTS

| | | | |
|---|---|---|---|
| 2,084,692 | 6/1937 | Little | 128/307 |
| 2,157,293 | 5/1939 | Lenta | 57/300 |
| 2,811,969 | 11/1957 | Shubert | 128/303 R |
| 2,817,336 | 12/1957 | Kravitz et al. | 128/253 |
| 3,062,212 | 11/1962 | Kravitz et al. | 128/253 |
| 3,587,591 | 6/1971 | Satterwhite | 128/361 |
| 3,620,676 | 11/1971 | Davis | 128/771 |
| 3,672,351 | 6/1972 | Ubersax et al. | 128/759 |
| 3,867,947 | 2/1975 | Schack | 128/361 |
| 4,199,882 | 4/1980 | Clayman | 128/771 |

*Primary Examiner*—Kyle L. Howell
*Assistant Examiner*—Nancy A. B. Swisher
*Attorney, Agent, or Firm*—Wood, Herron & Evans

[57] ABSTRACT

A medical testing device for determining whether the amniotic membrane has ruptured, and alternatively, for rupturing it. Finger-engaging means hold an elongated flexible member to the digits of a finger so as to be flexed when the finger is flexed. A lancet or hook is formed at one end of the flexible member, and projects angularly from it. The hook tip is engageable with a rupturable sac carried by the device. The sac contains a pH indicator which, when exposed to fluids in the cervix, changes color if the amniotic membrane has ruptured. The sac is ruptured by flexing the finger to tension the sac over the hook tip, so that the hook pierces the sac and exposes the pH indicator to the cervical fluid.

10 Claims, 4 Drawing Figures

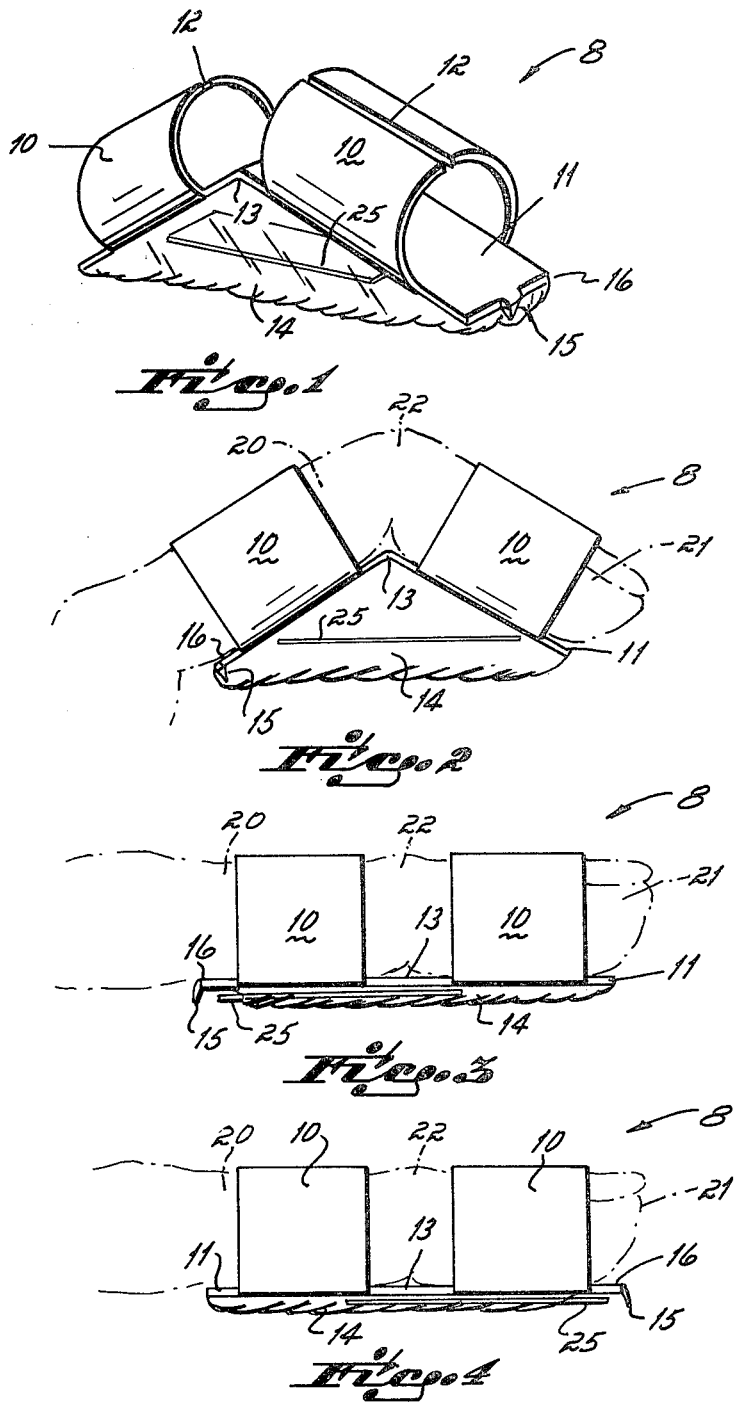

DEVICE FOR TESTING AND RUPTURING AMNIOTIC MEMBRANE

BACKGROUND OF THE INVENTION

This invention relates to a device for testing the intactness of the amniotic membrane, and for rupturing the membrane if desired.

Prior Art

Various devices have been designed to be worn on the finger with hooks or lancets at the tip for rupturing the amniotic membrane, see U.S. Pat. Nos. 2,084,694, 2,157,293 and 2,811,969. None of those devices is capable of both testing the local environment within the cervix to determine whether the amniotic membrane has broken, and also serving as an implement to rupture the membrane at the time of labor for inducing labor when necessary.

Diagnosis of the intactness of the amniotic membrane is extremely important during pregnancy. The membrane, when intact, serves as a primary barrier to the transportation of infectious or potentially infectious organisms or matter to the developing fetus in the womb. When ruptured, it is important that the fetus be promptly delivered to prevent injury or possible death. The present state of the medical art allows the live delivery of viable pre-mature infants from about 27-34 weeks in term, in facilities equipped with the most sophisticated infant life-support systems. Hospitals with pre-mature care units can typically handle fetuses in the 34-36 week of term, with normal hospital facilities capable of caring for pre-mature infants beyond the 36th week in term.

At present, one means available for testing the intactness of the amniotic membrane is by inserting some form of pH indicator into the immediate area of the womb, as by inserting a piece of litmus paper by means of forceps. This means of testing itself presents the risk of introducing infection into the womb through use of the forceps. Furthermore, the unprotected pH indicator can be exposed in its passage into the cervix to the more acidic fluid present in the vaginal area, thus rendering the indicator susceptible to a false reading of the intactness of the amniotic membrane.

It is an important feature of the testing device of this invention that it is capable of carrying a pH indicator into the region of the cervix in an unexposed condition to achieve a reliable and accurate indication of the presence of amniotic fluid. Once exposed, the indicator color is fixed and will not be altered through its passage out from the cervical area through the vaginal area. No less important is the ability of this disposable, pre-sterilized device to accomplish this test in a completely sterile manner, thereby reducing the risk of infection to the fetus in the event that the membrane has ruptured.

OBJECTS OF THE INVENTION

It has been the objective of this invention to provide a sterile, inexpensive, disposable, easily manipulated implement with a pH indicator that can selectively be exposed in situ within the cervix for determining whether the amniotic membrane has ruptured.

It has been another objective of the invention to provide a flexible member to be worn on the finger with a sharp lancet at one end, the lancet being employable for dual purposes, first for rupturing a sac containing a pH indicator in situ with the cervix for determining the presence of amniotic fluid and thus the intactness of the amniotic membrane, and secondly for rupturing the membrane itself in the event that it is unbroken and must be burst.

SUMMARY OF THE INVENTION

In accordance with the present invention, a bendable backing member carries finger tip-engaging means, such as circular clips into which the finger is inserted, to hold the backing member to the digits of a finger, on each side of a joint of the finger. The backing member is bendable transversely, at least at the approximate position of the joint between the second and third digits. The backing member is positioned on the top or the bottom side of the finger, so that it is flexed as the finger is bent.

An angular outwardly projecting lancet or hook is formed at one end of the backing member. Prior to use, the sharp tip of the lancet is positioned to engage, and preferably is enclosed within, a flexible sac which is mounted by the device adjacent the backing member. The sac may be of thin flexible plastic film, adhesively secured beneath the backing member. The lancet tip may project into the sac through an opening it is, sealed with adhesive. The sac contains a pH indicator which, when exposed to fluids in the cervix, changes color if the amniotic membrane is ruptured.

The pH value of an aqueous solution is a relative value describing its acidity or alkalinity. The pH of a neutral solution is 7, with a lower number indicating more acid solution, and a high number a more alkaline solution. The pH for the cervical area with the amniotic membrane intact would be in the range of 3.2-4.5. If the membrane is ruptured and amniotic fluid is present, the pH value would be expected to be in the 7.3-8 range. A widely used indicator such as phenapthazine has a suitable pH range for this test (about 4.5 to 8), and can be easily impregnated onto a paper strip or some other vehicle, such as cornstarch or talc, and carried within the sac. The plastic sac is made so that when the backing member is straightened by extension of the finger, the sac becomes first taut and then is ruptured by the lancet, thus exposing the indicator within the sac to the fluids of the cervix.

To perform the test for the presence of amniotic fluid, the testing device is preferably worn with the lancet end away from the fingertip, i.e. toward the palm of the hand. The finger is kept in a bent position, thus maintaining the device in roughly an inverted V-shape. The finger, carrying the device with its associated indicator-containing sac, is inserted into the cervix in this bent configuration. Once positioned within the cervix, the finger is straightened, thus causing the lancet to tear the plastic sac, exposing the indicator to local fluids within the cervix. The finger is then withdrawn, and the indicator examined for a coloration change indicative of the presence of amniotic fluid, thus establishing whether the membrane has indeed ruptured.

In the event that the membrane has not ruptured, and the onset of inducement of labor requires that it should be burst, the lancet is reversed on the finger, the hook portion now being located adjacent the fingertip. The flexible member can now be finger manipulated within the womb, with the lancet used to rupture the membrane.

BRIEF DESCRIPTION OF THE INVENTION

FIG. 1 is a perspective view of a device in accordance with the preferred embodiment of the invention in an "as supplied" condition.

FIG. 2 is a side elevation of the device of FIG. 1, as worn on the finger in an articulated, ready-for-testing attitude, with the lancet disposed rearwardly.

FIG. 3 is also a side elevation, showing the backing member straightened and the indicator sac ruptured by the lancet, so as to expose the pH indicator for testing intactness.

FIG. 4 is a view similar to FIG. 3 but with the device in a reversed position on the finger for rupturing an amniotic membrane.

DETAILED DESCRIPTION

Referring to FIG. 1, the testing device is designated generally by 8 and preferably has a flexible backing member 11 which carries means by which the device can be engaged with and carried on the outer end of the finger.

Preferably the device is carried on the second and third digits of the finger, 20 and 21 respectively. The finger will be gloved; the glove is omitted in the drawing for clarity. In the preferred form shown, the finger-engaging means comprises two upwardly extending, rounded clips 10, 10 projecting from backing member 11. The clips 10, 10 are designed to fit around and loosely grip the second 20 and third digits 21 of the finger, on each side of the joint between such digits. For this purpose clips 10 are advantageously split longitudinally as at 12, the splits permitting the clips to engage and grip fingers of different sizes. A weakened or "hinged" portion of the backing member 11 is preferably located approximately at the midpoint of the backing member, and provides a flexion line or hinge axis 13. For use on the index finger, the backing member may suitably be approximately 0.5 centimeters in width and 4 centimeters long, with the flexion point located at the 2 cm. midpoint. The clips 10,10 are located on opposite sides of hinge axis 13.

A sealed plastic envelope in the form of a sac 14 is attached to and carried below the backing member 11, and extends to an end 16 thereof. This sac 14 contains the pH indicator to be used for testing the presence of amniotic fluid in the cervix. In the embodiment shown the indicator is impregnated on a piece of paper 25; alternatively the indicator may be mixed with a powdered material such as cornstarch and a binder, and sprayed onto an inside surface of the sac.

A hook or lancet 15 is integral with the backing member and preferably is centrally located on the end 16. The hook 15 depends downwardly, projecting into and normally enclosed within the sac 14.

FIG. 2 shows the device of the invention as it would preferably be used on a finger for testing of the local fluids in the cervix. The device is supplied to the user in the depicted bent configuration. The user simply inserts a finger, typically the index finger, into the clips so that the clips 10 are positioned over the tip 21 and next innermost digit 22 of the finger, respectively, with the backing member so arranged that the hook 15 is located closest to the palm. In this position the hook is removed from the membrane, so that it cannot accidentally rupture the membrane. The hinge axis 13 lies beneath the finger's outer joint 22. Once in place on the finger, the apparatus is inserted into the cervix; the finger is then extended (FIG. 3). This causes a corresponding straightening of backing member 11, flexion occurring along the line 13. The plastic sac 14 is thereby drawn taut over hook 15 by the extension of the backing member 11, and then is punctured by the hook. The sac is thus opened to expose the pH indicator in it to the local fluids of the cervix. The apparatus is then withdrawn, and the indicator checked for an indication of the presence of amniotic fluid.

FIG. 3 shows the backing member 11 fully extended with the plastic sac 14 ruptured by the hook 15. If, for example, the indicator is phenapthazine, rupture of the amniotic membrane will increase the pH of the fluid, and will produce a color of the indicator in the sac.

In the event that the amniotic membrane has not yet ruptured, and it is desired that it be ruptured, the device is reversed on the finger (FIG. 4). The clips 10 are slid over the same proximal finger digits, but reversely so that the hook 15 is adjacent the fingertip, in position to engage the membrane. The device is then re-inserted within the cervix and manipulated by the finger to rupture the amniotic membrane with the lancet 15.

From the foregoing, it will be understood that this invention provides an implement useful both to test the fluids in the cervix for the presence of amniotic fluid indicative of the rupturing of the amniotic membrane, as well as selectively to rupture the amniotic membrane in the event that is desired. The device is disposable and inexpensive, and is capable of being reversably worn on a finger, thus making it convenient for implacement and manipulation within the cervix. The self-contained selectively exposible pH indicator carried by the device can be exposed within the cervix only, so as to respond only to those fluids located in the local environment of the cervix.

It should be understood that although the foregoing embodiment is preferably worn on the ventral (palm) side of the finger, it can also be adapted to be worn on the other or dorsal side as well. In the latter case, the flexible sac containing the indicator is positioned on the upward side of the backing member, in an unstressed condition with the finger straightened. Upon flexing the finger, and correspondingly the backing member, the sac is brought taut over the lancet and then ruptured, thereby exposing the indicator to local fluids.

Further, it should also be understood that the backing member described herein need not constitute a flat element, nor need it be formed of a single piece. The finger engaging means can comprise a sheath, rather than the clips shown.

Various changes in the forms of this invention herein described and illustrated may be made without departure from the spirit of the invention and the scope of the claims which follow.

What is claimed is:

1. A device for testing for the presence of amniotic fluid in the cervix, thereby to indicate the intactness of the amniotic membrane, comprised of:
    a backing member sized to fit, in use, longitudinally adjacent a joint of a finger, said backing member being laterally flexible at at least one point thereof which in use is adjacent to said joint of the finger,
    means for removeably attaching said backing member to said finger,
    a flexible sac affixed to and carried by said backing member, said sac containing a pH indicator responsive to the presence of amniotic fluid, and sac-piercing means affixed to said device adjacent said sac, said piercing means positioned to engage and rupture said sac when said sac is drawn taut over said piercing means when said finger is flexed at said joint, thereby exposing the pH indicator inside said sac to local fluids in the area of the cervix.

2. The device of claim 1 wherein said piercing means is a lancet which extends angularly from one end of said backing member.

3. The device of claim 1 wherein said lancet extends from said backing member into said sac through a sealed opening in said sac.

4. The device of claim 1 wherein said backing member has a transverse hinge axis approximately at its mid-point.

5. The device of claim 1 wherein said device can be worn reversably on said finger.

6. The device of claim 1 wherein said removable attaching means comprises at least one clip for at least partially encircling one of the digits of the finger.

7. The device of claim 6 wherein two such clips are provided on said backing member, for engaging the 2nd and 3rd digits of the finger in use, on either side of said joint.

8. The device of claim 1 wherein said flexible sac is made of plastic film piercible by said lancet.

9. The device of claim 1 wherein said flexible sac is adhesively secured to said backing member on a side thereof which is opposite from said finger.

10. The device of claim 1 wherein said backing member has a hinge axis positioned so that when said device is positioned on said finger, said hinge axis will be adjacent to the outer joint of said finger.

* * * * *